US008535025B2

(12) United States Patent
Rotem et al.

(10) Patent No.: US 8,535,025 B2
(45) Date of Patent: Sep. 17, 2013

(54) MAGNETICALLY BALANCED FINGER-TYPE PERISTALTIC PUMP

(75) Inventors: Shachar Rotem, M.P. Hefer (IL); Ori Goldor, Amikam (IL)

(73) Assignee: Q-Core Medical Ltd., Netanya (IL)

( * ) Notice: Subject to any disclaimer, the term of this patent is extended or adjusted under 35 U.S.C. 154(b) by 640 days.

(21) Appl. No.: 12/463,399

(22) Filed: May 10, 2009

(65) Prior Publication Data

US 2009/0240201 A1 Sep. 24, 2009

Related U.S. Application Data

(63) Continuation-in-part of application No. PCT/IL2007/001400, filed on Nov. 13, 2007, and a continuation-in-part of application No. PCT/IL2007/001402, filed on Nov. 13, 2007.

(30) Foreign Application Priority Data

Nov. 13, 2006 (IL) .......................................... 179229
Nov. 13, 2006 (IL) .......................................... 179232

(51) Int. Cl.
*F04B 43/12* (2006.01)

(52) U.S. Cl.
USPC .......................... 417/477.1; 417/474; 417/374

(58) Field of Classification Search
USPC ................. 417/477.3, 477.7, 474, 476, 477.1, 417/374; 74/25, 54, 55
See application file for complete search history.

(56) References Cited

U.S. PATENT DOCUMENTS

| 2,056,322 | A | | 10/1936 | Hoppe |
| 2,743,898 | A | | 5/1956 | King |
| 2,981,115 | A | * | 4/1961 | Beguin ............................. 74/25 |
| 3,443,585 | A | | 5/1969 | Reinicke |
| 3,982,722 | A | | 9/1976 | Bernard |
| 3,982,725 | A | | 9/1976 | Clark |
| 4,014,318 | A | * | 3/1977 | Dockum et al. ................ 600/16 |
| 4,039,269 | A | | 8/1977 | Pickering |

(Continued)

FOREIGN PATENT DOCUMENTS

| DE | 10118086 A | 7/2002 |
| EP | 0215249 A1 | 3/1987 |

(Continued)

OTHER PUBLICATIONS

U.S. Appl. No. 12/644,027 Official Action dated Apr. 28, 2011.

(Continued)

*Primary Examiner* — Charles Freay
*Assistant Examiner* — Alexander Comley
(74) *Attorney, Agent, or Firm* — Vladimir Sherman; Professional Patent Solutions

(57) ABSTRACT

A peristaltic pump includes a plurality of effecters, actuated in a periodic manner upon by obstructive forces of a flexible infusion tube so as flow of infusion fluid is provided along said infusion tube, the magnitude of the obstructive forces being dependent upon the displacement of said moving effecters; and a plurality of balancing magnets providing balancing forces upon one or all the moving effecters, the balancing forces at each point along the path of motion of the moving effecters being of approximately equal magnitude to that of the obstructive forces at the point; such that the parasitic output due to work performed against the obstructive forces is approximately zero and yield is maximized.

8 Claims, 6 Drawing Sheets

(56) References Cited

U.S. PATENT DOCUMENTS

| | | | | |
|---|---|---|---|---|
| 4,155,362 | A | 5/1979 | Jess | |
| 4,236,880 | A | 12/1980 | Archibald | |
| 4,270,532 | A | 6/1981 | Franetzki et al. | |
| 4,320,781 | A | 3/1982 | Bouvet et al. | |
| 4,373,525 | A * | 2/1983 | Kobayashi | 417/63 |
| 4,450,375 | A | 5/1984 | Siegal | |
| 4,489,863 | A | 12/1984 | Horchos et al. | |
| 4,682,135 | A | 7/1987 | Yamakawa | |
| 4,690,673 | A * | 9/1987 | Bloomquist | 604/67 |
| 4,728,265 | A * | 3/1988 | Cannon | 417/363 |
| 4,741,736 | A | 5/1988 | Brown | |
| 4,836,752 | A * | 6/1989 | Burkett | 417/12 |
| 4,867,744 | A * | 9/1989 | Borsanyi | 604/153 |
| 4,893,991 | A | 1/1990 | Heminway et al. | |
| 4,978,335 | A | 12/1990 | Arthur, III | |
| 5,096,385 | A | 3/1992 | Georgi et al. | |
| 5,103,211 | A * | 4/1992 | Daoud et al. | 340/608 |
| 5,152,680 | A | 10/1992 | Okada | |
| 5,213,483 | A | 5/1993 | Flaherty et al. | |
| 5,257,978 | A | 11/1993 | Haber et al. | |
| 5,286,176 | A * | 2/1994 | Bonin | 417/413.1 |
| 5,290,158 | A | 3/1994 | Okada | |
| 5,395,320 | A | 3/1995 | Padda et al. | |
| 5,509,439 | A | 4/1996 | Tantardini | |
| 5,527,295 | A | 6/1996 | Wing | |
| 5,575,309 | A | 11/1996 | Connell | |
| 5,577,891 | A | 11/1996 | Loughnane et al. | |
| 5,593,134 | A | 1/1997 | Steber et al. | |
| 5,658,252 | A | 8/1997 | Johnson | |
| 5,660,529 | A * | 8/1997 | Hill | 417/53 |
| 5,683,233 | A | 11/1997 | Moubayed et al. | |
| 5,782,805 | A | 7/1998 | Meinzer et al. | |
| 5,807,322 | A | 9/1998 | Lindsey et al. | |
| 5,888,052 | A * | 3/1999 | Hill | 417/53 |
| 5,896,076 | A | 4/1999 | van Namen | |
| 5,996,964 | A | 12/1999 | Ben-Shalom | |
| 6,095,189 | A | 8/2000 | Ben-Shalom | |
| 6,164,921 | A | 12/2000 | Moubayed et al. | |
| 6,165,874 | A | 12/2000 | Powell et al. | |
| 6,203,296 | B1 | 3/2001 | Ray et al. | |
| 6,213,739 | B1 * | 4/2001 | Phallen et al. | 417/478 |
| 6,261,262 | B1 | 7/2001 | Briggs et al. | |
| 6,339,410 | B1 | 1/2002 | Milner et al. | |
| 6,371,732 | B1 * | 4/2002 | Moubayed et al. | 417/44.1 |
| 6,450,773 | B1 | 9/2002 | Lipton | |
| 6,537,244 | B2 | 3/2003 | Paukovits et al. | |
| 6,692,241 | B2 * | 2/2004 | Watanabe et al. | 417/477.2 |
| 6,733,476 | B2 * | 5/2004 | Christenson et al. | 604/151 |
| 7,018,361 | B2 | 3/2006 | Gillespie, Jr. et al. | |
| 7,022,075 | B2 | 4/2006 | Grunwald et al. | |
| 2002/0156402 | A1 | 10/2002 | Woog et al. | |
| 2002/0165503 | A1 | 11/2002 | Morris et al. | |
| 2003/0040700 | A1 | 2/2003 | Hickle et al. | |
| 2003/0182586 | A1 | 9/2003 | Numano | |
| 2004/0181314 | A1 | 9/2004 | Zaleski | |
| 2005/0088409 | A1 | 4/2005 | Van Berkel | |
| 2005/0112001 | A1 * | 5/2005 | Bahnen et al. | 417/418 |
| 2006/0051218 | A1 * | 3/2006 | Harttig | 417/412 |
| 2007/0048161 | A1 * | 3/2007 | Moubayed | 417/477.1 |
| 2007/0154336 | A1 * | 7/2007 | Miyazaki et al. | 417/474 |
| 2007/0269324 | A1 | 11/2007 | Goldor et al. | |
| 2008/0065016 | A1 * | 3/2008 | Peterson et al. | 604/151 |
| 2008/0095649 | A1 | 4/2008 | Ben-Shalom et al. | |

FOREIGN PATENT DOCUMENTS

| | | | |
|---|---|---|---|
| EP | 0225158 | A2 | 6/1987 |
| FR | 2632529 | A | 12/1989 |
| JP | 60043188 | A | 3/1985 |
| JP | 6-169992 | A | 6/1994 |
| JP | 2002-57738 | A | 2/2002 |
| JP | 2004141418 | A | 5/2004 |
| WO | 9116933 | A1 | 11/1991 |
| WO | 03027503 | A1 | 4/2003 |
| WO | 2008059492 | A2 | 5/2008 |
| WO | 2008059493 | A2 | 5/2008 |
| WO | 2008059494 | A2 | 5/2008 |
| WO | 2008059495 | A2 | 5/2008 |
| WO | 2008059496 | A2 | 5/2008 |
| WO | 2008059498 | A2 | 5/2008 |
| WO | 2008059499 | A2 | 5/2008 |

OTHER PUBLICATIONS

U.S. Appl. No. 11/791,599 Official Action dated Mar. 31, 2011.
European Patent Application # 10192477.7 Search Report dated May 10, 2011.
U.S. Appl. No. 10/535,103 Official Action dated Feb. 2, 2009.
International Application PCT/IL2007/001398 Search Report dated Jun. 11, 2008.
International Application PCT/IL2007/001398 Patentability Report dated May 28, 2009.
International Application PCT/IL2007/001399 Search Report dated Jun. 4, 2008.
International Application PCT/IL2007/001399 Patentability Report dated May 19, 2009.
International Application PCT/IL2007/001400 Search Report dated Jul. 15, 2008.
International Application PCT/IL2007/001400 Patentability Report dated May 28, 2009.
International Application PCT/IL2007/001401 Search Report dated Sep. 24, 2008.
International Application PCT/IL2007/001401 Patentability Report dated May 28, 2009.
International Application PCT/IL2007/001402 Search Report dated Jun. 20, 2008.
International Application PCT/IL2007/001402 Patentability Report dated May 28, 2009.
International Application PCT/IL2007/001404 Search Report dated Jul. 14, 2008.
International Application PCT/IL2007/001404 Patentability Report dated May 28, 2009.
International Application PCT/IL2007/001405 Search Report dated Jul. 21, 2008.
International Application PCT/IL2007/001405 Patentability Report dated May 28, 2009.
International Application PCT/IL2005/001249 Search Report dated Apr. 5, 2006.
International Application PCT/IL2003/000947 Search Report dated Mar. 3, 2004.
Chinese Patent Application No. 200580045471.3 "Finger-type peristaltic pump" Official Action dated Jul. 18, 2008.
U.S. Appl. No. 09/125,438 Official dated May 3, 1999.
U.S. Appl. No. 09/125,438 Official dated Jul. 15, 1999.
European Application No. 05810500.8 Official Action dated Jul. 6, 2009.
International Application PCT/IL1997/000289 Search report dated Jan. 27, 1998.
International Application PCT/IL1997/000290 Search Report dated Jan. 27, 1998.
U.S. Appl. No. 12/464,202 Official Action dated Oct. 3, 2011.
U.S. Appl. No. 12/514,310 Official Action dated Jul. 21, 2011.

* cited by examiner

| | Stage 1 | Stage 2 | Stage 3 | Stage 4 | |
|---|---|---|---|---|---|
| Finger 4 | | | | | Tube loosened / Tube compressed |
| Finger 3 | | | | | Tube loosened / Tube compressed |
| Finger 2 | | | | | Tube loosened / Tube compressed |
| Finger 1 | | | | | Tube loosened / Tube compressed |
| Cycle | T/4 | T/4 | T/4 | T/4 | |

*Fig. 3*

MAGNETICALLY BALANCED FINGER-TYPE PERISTALTIC PUMP

CROSS-REFERENCE TO RELATED APPLICATIONS

This application is a continuation-in-part of PCT patent applications PCT/IL2007/001400 and PCT/IL2007/001402, both filed Nov. 13, 2007, and both of which are incorporated herein by reference.

FIELD OF THE INVENTION

The present invention generally relates to a magnetically balanced finger-type peristaltic pump, especially a pump comprising at least one tailor made cam.

BACKGROUND OF THE INVENTION

This invention relates to designs for cams to operate magnetically balanced fingers of a peristaltic pump. At present peristaltic pumps find use in medical settings to add nutrients to blood, to force blood through filters to clean it as in dialysis, or to move blood through the body and lungs during open heart surgery. They are advantageous in these situations since the pump elements do not contact the pumped fluid, eliminating any possibility of contamination. Additionally the pumping action may be gentle enough that blood cells are not damaged. Further uses include pumping aggressive chemicals, high solids slurries and other materials where isolation of the product from the environment, and the environment from the product, are critical. As the operation of such a pump can be critical for life support, they are generally provided with battery backup. The efficiency of the device thus becomes an important parameter since the length of time it can remain in operation while on battery power is limited by its efficiency.

A common arrangement for the operation of a peristaltic pump is shown in the prior art of FIG. 1 (100 is a front view and 101 is a lateral view), wherein a plurality of fingers 104 press the feed tube 103 against a substrate 105 by means of a cam 102. Neighboring fingers are operated in sequence such that a squeezing or 'peristaltic' motion operates along the length of the tube, forcing the contents of the tube in one direction. By adjusting the speed of rotation of the cams, the speed of pumping can be adjusted.

In U.S. Pat. No. 4,725,205 a mechanically compensated cam for use in a peristaltic pump is disclosed. The system described uses specially designed cams that reduce the maximum force applied between fingers 104 and tube 103 by means of a compliant spring. In this manner problems of jamming due to poor alignment or out-of-tolerance tubes are eliminated. This system while effective and simple involves a certain amount of wasted energy as will be described below. Furthermore, being based on an eccentric circle, the fingers follow a trajectory sinusoidal in nature, which limits the volume pumped per camshaft revolution. Varying the trajectory from that of a sinusoid would offer the benefit of fixing the duration during which the tube is shut off, allowing for an increase in the volume pumped per revolution.

Thus a design and method for the cam of a peristaltic pump allowing a tailored finger trajectory that reduces the probability of jamming in out-of-tolerance tubes, as well as allowing increased volume per rotation and subsequent enhanced energy savings is a long felt need.

BRIEF DESCRIPTION OF THE DRAWINGS

In order to understand the invention and to see how it may be implemented in practice, a plurality of embodiments will now be described, by way of non-limiting example only, with reference to the accompanying drawings, in which

FIG. 3 schematically presents the state of each finger at each of the four steps of a single pumping cycle wherein at each step, two fingers are static and two are moving;

SUMMARY OF THE INVENTION

Figure 1:
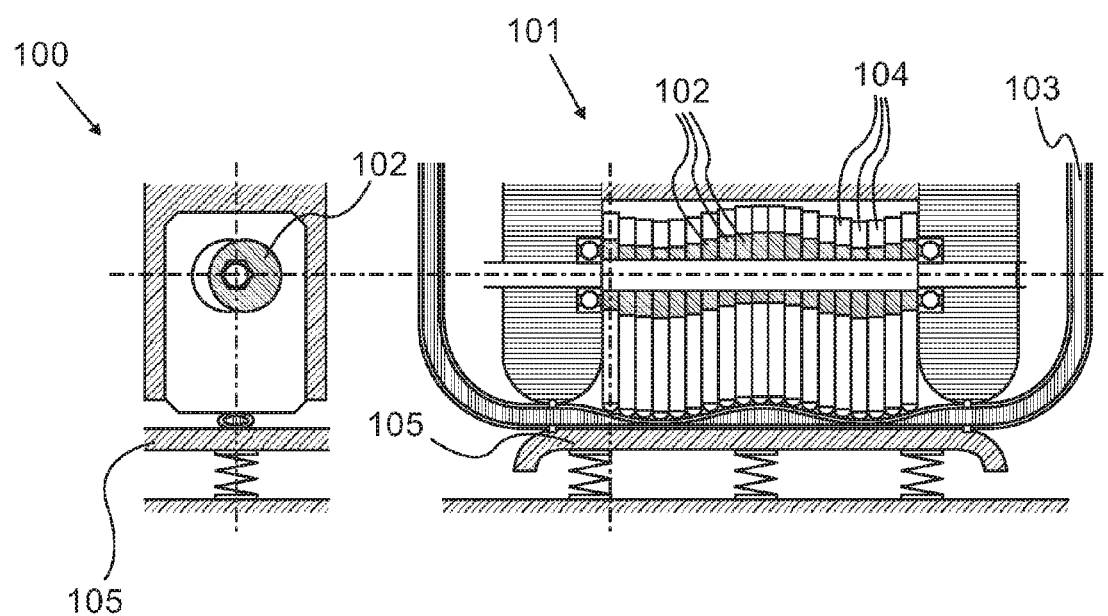
FIG. 1 shows in prior art a typical peristaltic pump making use of fingers 104 pressing against a uniform substrate 105.

In some embodiments a finger-type peristaltic pump (DDS) comprising a plurality of pressing-fingers, actuated in a periodic manner upon by obstructive forces of a flexible infusion tube so as peristaltic flow of infusion fluid is provided along said infusion tube, the magnitude of said obstructive forces being dependent upon the displacement of said moving finger; and a plurality of balancing magnets providing balancing forces upon said moving fingers, said balancing forces at each point along the path of motion of the moving member being of approximately equal magnitude to that of said obstructive forces at the point; such that the parasitic output due to work performed against said obstructive forces is approximately zero and yield is maximized.

A magnetically balanced finger-type peristaltic pump as defined above may be especially adapted to be utilized as ambulatory and hospital infusion pumps.

In some embodiments, a magnetically balanced finger-type peristaltic pump is defined as above wherein at least a portion of said plurality of pressing-fingers is magnetically balanced and wherein each of said magnetically balanced pressing-fingers comprises one or more magnets stacked in the direction of said pressing by means of one or more metal members, said metal member is optionally selected from ferromagnetic materials, fixed magnets, static magnets that are nor actuated in respect to the pressing-fingers or any combination thereof.

In some embodiments, the magnets are not located on the pressing fingers. Hence, at least a portion of the magnets are located in sides of the fingers, whereas iron or other magnetic materials are located on the fingers.

In some embodiments, a magnetically balanced finger-type peristaltic pump is defined as above, wherein each of said magnetically balanced pressing-fingers of linear movement is actuated periodically by a rotating cam towards a flexible infusion tube i.e., until a complete yet temporary shut off of said tube is obtained, and backwards, i.e., until said fingers are not pressing said tube; wherein said magnetic balance avoids significant pressing forces between said cam and said fingers.

In some embodiments, the pressing fingers maneuver along a non-linear movement, e.g., a curved movement etc.

In some embodiments, a magnetically balanced finger-type peristaltic pump is defined as above wherein said magnetic balance avoids significant pressing forces between said cam and said fingers along their entire forth and backwards linear movement. It is acknowledged in this respect that the force between the finger and the cam is negligible due to the balancing magnet force yielding almost no friction on the cam surface. As a result, no torque evolves on the cam and almost no energy is needed to rotate the pumping mechanism.

In some embodiments, a magnetically balanced finger-type peristaltic pump is defined as above wherein said fingers remain at maximum extension for a large angular sweep $\Delta\theta$ of the shaft, such as 87.5°, causing complete tube shutoff during said large and predetermined range.

In some embodiments, a magnetically balanced finger-type peristaltic pump is defined as above, comprising inter alia a plurality of N pressing fingers, N is any integer number higher 2, especially 4, wherein per any given pumping cycle, each of said fingers are in one of two alternating states of being either static or moving (or approaching to movement); in said static state said at least one finger is pressing said flexible infusion tube and at least one finger is withdrawn and not pressing said tube; in said moving state at least one finger is withdrawing from said tube and at least one finger is pressing the same.

In some embodiments, a magnetically balanced finger-type peristaltic pump is defined as above, wherein the static and moving states of said fingers per any given pumping cycle are as defined in FIG. 3.

In some embodiments a magnetically balanced finger-type peristaltic pump is defined as above, wherein at least a portion of said cams are characterized by one or more crescent forms, each of which of said crescent forms is adapted to provide pressing of said finger by magnetic forces of said balancing magnets in the manner that said magnetic forces are at least slightly stronger than the oppositely directed elastic forces, provided by the squeezing of said flexible tube by said finger while shutting off said tube; by applying said magnetic force, complete tube's shut off is assured, especially in cases of worn out tubes and pumping mechanisms with noticeable tolerances.

In some embodiments, a magnetically balanced finger-type peristaltic pump is defined as above wherein at least a portion of said cams are characterized by a first and a second crescent forms located in opposite directions: The first crescent form is adapted to provide pressing of said finger by magnetic forces of said balancing magnets in the manner that said magnetic forces are at least slightly stronger than the oppositely directed elastic forces, provided by the squeezing of said flexible tube by said finger while shutting off said tube; by applying said magnetic force, complete tube's shut off is assured. The second crescent form is adapted to provide additional finger movement in the direction of withdrawing said tube, so as complete tube's after-press inflation is assured, especially in cases of worn out tubes, wider tubes, tubes of wider walls, and pumping mechanisms with noticeable tolerances.

In some embodiments, a magnetically balanced finger-type peristaltic pump is defined as above wherein the pressing-finger are of rounded cross sections, additionally comprising sealing means that hermetically barriers between proximal portion of the fingers, i.e., the portion constantly located inside said pump's housing, and distal portion of said fingers, i.e., the pressing tip located outside said housing; said sealing means is especially selected from O-rings, U-rings or the like.

The magnetically balanced finger-type peristaltic pump as defined above is especially useful for reduce pumping energy and provide extended working time per given set of batteries. The system reduces mechanical wear of moving members, especially of cams and fingers. Less tube degradation is provided in the system. Scaling down is facilitated by reducing sizes of both engine and gear mechanism. Tube wear out is reduced, while improved accuracy is provided due to decrease degradation. The aforesaid pumping system also provides use of pumping mechanisms of bigger tolerances in production and assembly. The system provides for improved mechanical efficiency and allows use of sealed pressing-fingers so as sealed pump is obtained, and less sensitivity is obtained to dirt and contaminated body fluids. Lastly, the patented pumping system provides for downstream pressure built up without any requirements of applying high pumping moments.

In some embodiments, the peristaltic pump is defined as above, wherein at least a portion of said balancing magnets is located in a location selected from a group consisting of the elongated body portion of the finger-type pressing members (fingers), the fingers block or any combination thereof.

In some embodiments, the peristaltic pump is defined as above, wherein at least a portion of said balancing magnets comprises metal and other paramagnetic materials which location is one or more of a group consisting of in one or more portions of the finger-type pressing members (fingers), on one or more portions of the fingers, in the fingers block, on the fingers block or any combination thereof.

In some embodiments, at least a portion of said magnetically balanced pressing-fingers are actuated in at least partially non-linear movement.

In some embodiments, the magnetic force is applied in one or more specific points along the circumference of the rotating cam.

DETAILED DESCRIPTION OF PREFERRED EMBODIMENTS

The following description is provided so as to enable any person skilled in the art to make use of said invention and sets forth the best modes contemplated by the inventor of carrying out this invention. Various modifications, however, will remain apparent to those skilled in the art, and are considered to be within the scope of the present invention.

The terms 'about' or 'approximately' apply hereinafter to any value in a range from below 30% of a specified value to above 30% of said value.

The terms 'parasitic input' and 'parasitic output' apply hereinafter in the manner that parasitic input refers to the energy consumed by the system to produce parasitic output. The parasitic input is greater than the parasitic output because of internal losses. For example, an elevator with a cabin of weight 10,000 N being used to raise a man of weight 700 N through 10 m produces 107 kJ of output of which only 7 kJ are necessary output the remaining 100 kJ are parasitic output due to raising the cabin itself.

The term 'effecters' refers hereinafter to any portion of a device whose position changes during the working of the device, such as pressing fingers, peristaltic rollers etc.

The term 'necessary output' applies hereinafter to the energy needed to be produced by a system in order to perform the task for which the system is designed. For example in order perform the task of raising a man of weight 700 N through 10 m the necessary output of a system such as an elevator is 7 kJ of energy.

The term 'obstructive forces' refers hereinafter to any force which acts upon a moving member during its movement. More specifically this term is used to refer to forces dependent upon the displacement of a moving member.

The term 'output' applies hereinafter to energy produced by a system.

The term 'actuated in a periodic manner' applies hereinafter to any system wherein at least one component or effecter performs a series of steps repeatedly a plurality of times.

It is in the scope of the present invention to introduce the tailored cam, whose radius is not a circle rotating about an eccentric axis, but rather varies in such a manner that the fingers remain closed for a large sweep of the shaft, such as 87.5° out of the full 360° of rotation. The unique profile of the tailored cam allows complete tube shutoff during this large and predetermined range, preventing backflow through this entire range and allowing subsequent fingers a longer range of shaft angle θ in which to effect their peristaltic motion. This has an effect of decreasing the noise of the peristaltic pump, decreasing the energy consumption and effectively obtaining the conditions defined in the figures, e.g., FIG. 6.

It is furthermore within the scope of the present invention that a reduced-radius 'compliance zone' be included in the design of the cam, to accommodate tubes of increased diameter that would not otherwise be allowed to open completely. An out-of-compliance tube with increased diameter would remain partially closed even during the fingers' 'open' range but for the inclusion of the reduced radius 'compliance zone'. This partial closure would impede the free flow of fluid through the tube, reducing the throughput of the pump in such cases.

It is furthermore within the scope of the present invention and according to one specific embodiment of the same, wherein the aforementioned advantages are provided while still minimizing the first, second, and third derivatives of radius with shaft angle θ. The first derivative directly controls the finger velocity, and thus influences the kinetic energy invested therein. The second derivative affects the force upon the tube, which it is desirable to reduce insofar as possible in order to eliminate jamming, tube rupture, or disturbance of the fragile materials such as human cells passing through the tube. The third derivate controls the 'jerk' of the finger, which it is desirable to minimize since the jerk causes undue stress and strains on the cam, introduces vorticities into the flow, and causes vibration and noise.

It is in the scope of the invention wherein the cam comprises single, double or more crescent forms. Hence for example, a crescent form located at the wide radius of the cam avoids a long pressing period where a continuous strong pressure is applied upon the tube. The magnetic forces are pressing the tube. Along this crescent form, the cam is minimally touching the pressing fingers and hence the force for rotating the cam is provided with a minimal measure. Similarly and as another example of one mode of the invention, a crescent form located at the short radius of the cam provides the cam with another possible movement, which is especially useful (i) in tubes with degradated walls; (ii) in pressing mechanism with noticeable production or assembly tolerances; (iii) in using tubes with relatively thin walls; (iv) or in cases of insufficient pressing forces. Those cases are characterized by unsealed tubes, whereat leaking is possible.

Figure 2:
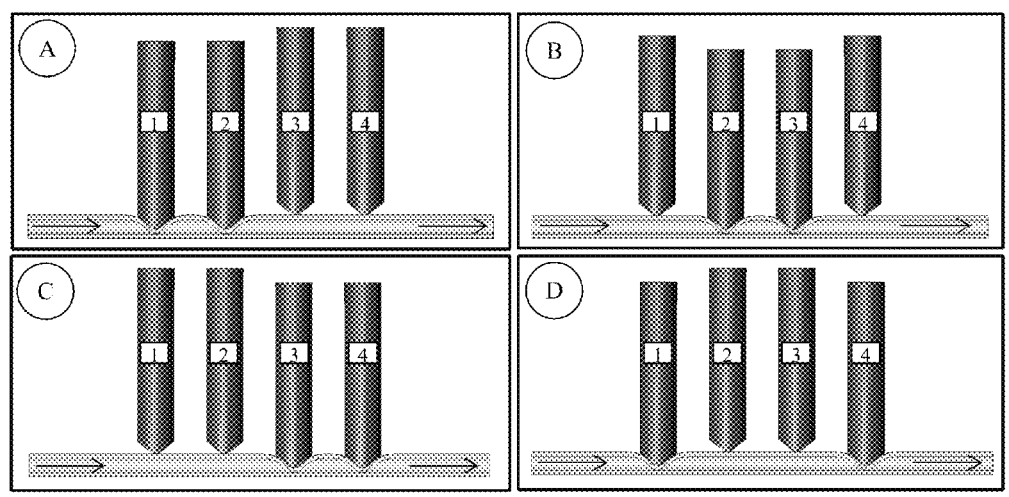
FIG. 2 schematically illustrating the fingers location at each of the four steps of the pumping cycle of a pumping mechanism comprising of four fingers.

Reference is now made to FIG. 2, which illustrates the fingers location at each of the four steps of the pumping cycle of a pumping mechanism comprising of four fingers. FIG. 3 schematically presents the state of each finger at each of the four steps of a single pumping cycle wherein at each step, two fingers are static and two are moving. It is yet according to one embodiment of the invention wherein the rotating cams are designed in a manner that a predefined overlap (e.g., 3%) between adjacent stages is obtained. Hence, one finger is switched from open configuration (tube loosed) to close configuration (tube compressed) only after a short while where an adjacent finger is switched to its close configuration.

Figure 4:
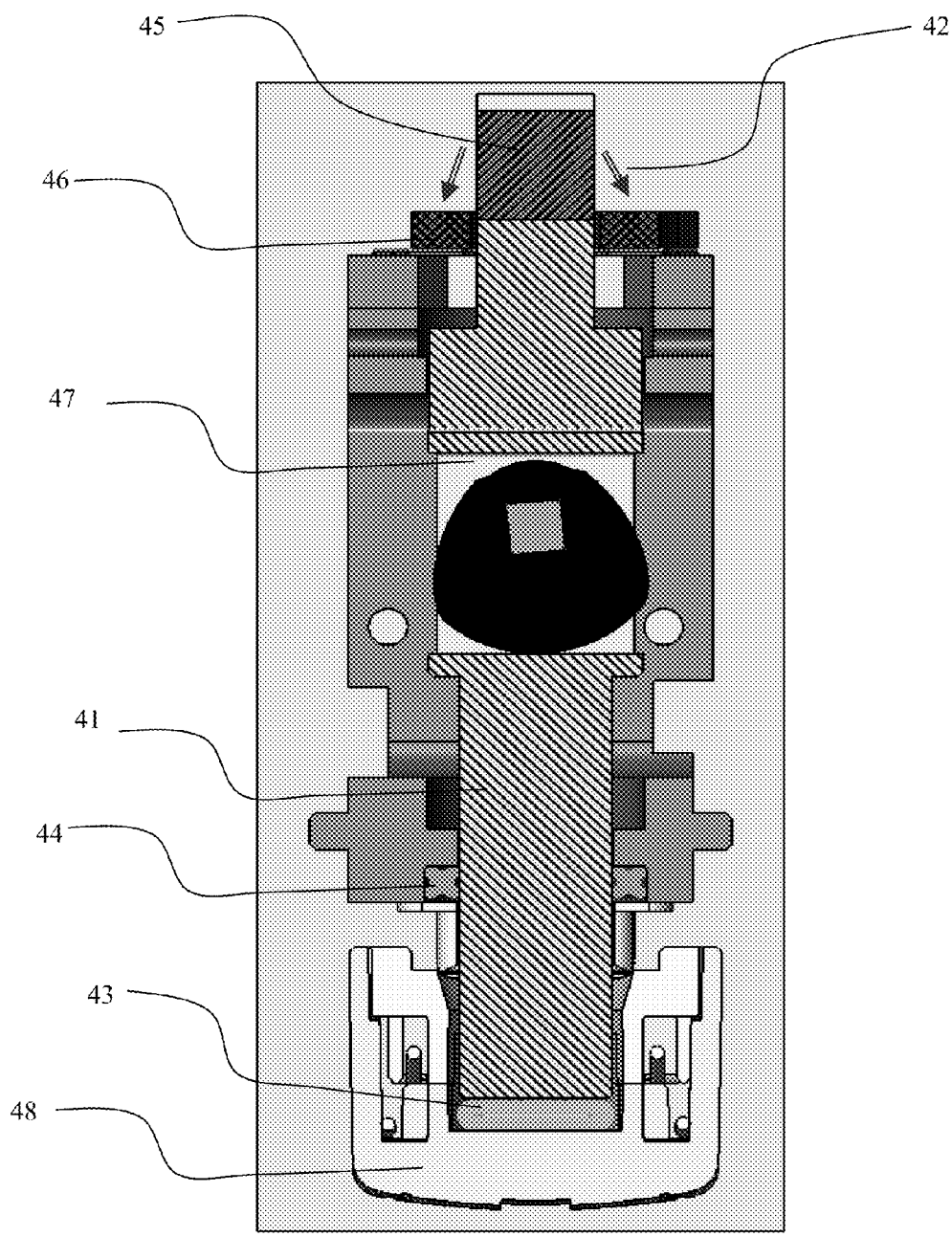
FIG. 4 schematically presents a cross section of the pumping mechanism according to one embodiment of the invention, wherein one portion of the cams is characterized by one crescent form.

Reference is now made to FIG. 4 which schematically presents a cross-section of a pumping mechanism according to one embodiment of the invention. FIG. 4 specifically illustrating one portion of the cams is characterized by one crescent form, adapted to provide pressing of a finger (41), e.g., via a seal (44), by magnetic forces (42) of the balancing magnets in the manner that the magnetic forces are at least slightly stronger, than the oppositely directed elastic forces, provided by the squeezing of the flexible tube by the finger while shutting off the tube (43) against a base (48); by applying the magnetic force, complete tube's shut off is assured, especially in cases of worn out tubes and pumping mechanisms with noticeable tolerances; this pumping mechanism with magnetically balances pressing fingers 41 is provided with preset balancing forces at each point along the path of motion of the moving fingers being of approximately equal magnitude to that of said obstructive forces at this point; such that the parasitic output due to work performed against the obstructive forces is approximately zero and yield is maximized. The pumping mechanism further comprises a magnet (45), ferromagnetic metal (46), and a cam (47a). Here for example, cam 47a is characterized by a single crescent form.

Figure 5:
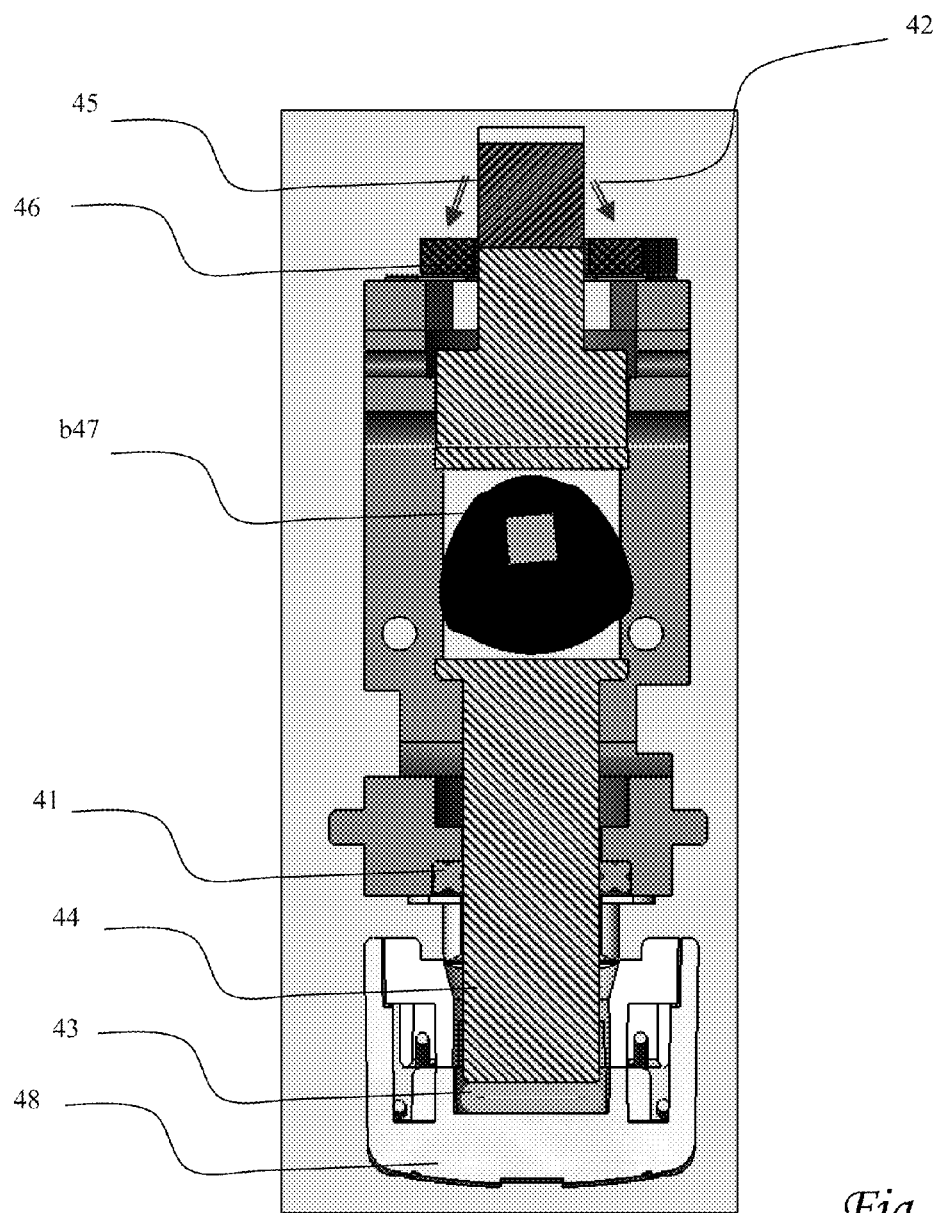
FIG. 5 schematically presents a cross section of the pumping mechanism according to one embodiment of the invention, wherein one portion of the cams is characterized by two crescent forms.
Figure 6:
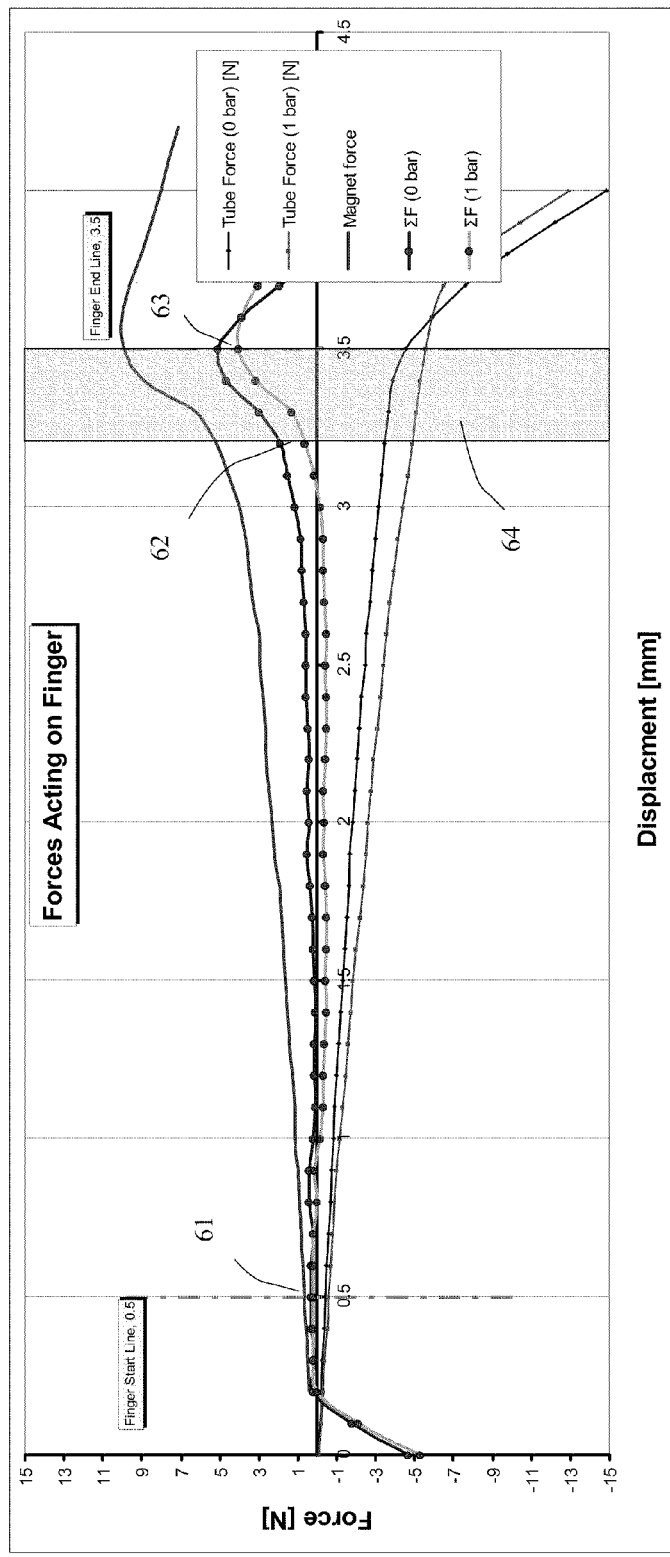
FIG. 6 graphically presents the forces on a single finger applied along a single half pumping cycle.

Reference is now made to FIG. 5, which schematically presents a cross-section of another pumping mechanism according to the present invention, comprises inter alia a magnet 45, ferromagnetic metal 46, and first crescent form of cam 47b which is adapted to provide pressing of finger 41 via a seal (44) by magnetic forces 42 of the balancing magnets in the manner that the magnetic forces are at least slightly stronger, than the oppositely directed elastic forces, provided by the squeezing of flexible tube 43 against a base (48) by the finger while shutting off the tube; by applying said magnetic force, complete tube's shut off is assured; the second crescent form is adapted to provide additional finger movement in the direction of withdrawing the tube, so as to facilitate a more relaxed form of mechanical pressure on the tube walls, especially in wider tubes, tubes of wider walls, and pumping mechanisms with noticeable tolerances; the said more relaxed form of mechanical pressure on the tube enable a prolonged life of the tube and as a consequence a more accurate flow rate throughout the pumping; and, Reference is now made to FIG. 6, which graphically presents the forces on a single finger applied along a single half pumping cycle; wherein point No. 1 symbols the upper point at with the finger tip is reaching through the pumping cycle. At this point almost no force is applied on the tube walls tube walls and the magnet was designed to apply equal small force on the finger so the total force acting between the cam and the finger is zero.

Point 2 denotes for the point in which the finger presses the tube to a flow shut off position; in this point, the magnetic force is greater than the obstructive force applied by the elastic tube so as shut off of the flow is assured at any pressure existing in the tube (up to 1 bar in this sample). At this point the magnet was designed to apply grater force then the force applied by the tube on the finger. This armament facilitates secured shut off of the tube under variant condition with very little total force acting on the finger, i.e. force acting between the cam and the finger is very small leading to decries in wear, energy consumption etc.

Point 3 represents the total force acting on the fingers which is slightly greater due to slightly greater magnetic forces. This design ensures complete shut off (squeeze) of the tube in case where tube walls degradation is presented or in case where a tube with inadequate walls thickness is used.

From this point the magnet force acting on the finger decreases to avoid puncturing of the tube.

Point 4 symbols the free movement of the finger to ensure complete shut off of the tube, especially in case of degradation of tube's walls, tolerances in pumping mechanism etc. ΣF is the total force applied on the finger in the direction of the press, i.e., the magnetic power minus obstructive forces of the elastic tube; the force applied by the cam on the pressing finger approx. equals the aforesaid force plus the forces required to overcome frictions in the pumping system. Point 4 hence describes the point whereat the magnetic forces are stronger than the elastic forces of the tube, such that the tube is effectively sealed.

The invention claimed is:

1. A peristaltic pump comprising:
    a channel to receive a flexible tube;
    at least one effecter including a metal member and adapted to intermittently compress the tube within said channel, wherein compression of the tube produces a reactive force;
    at least one electrically triggerable actuator to apply a mechanical force on said effecter; and
    a balancing member to magnetically interact with said metal member in said at least one effecter so that a balancing force proportional to the mechanical force on said effecter is produced to substantially counter said reactive force of the tube.

2. The peristaltic pump as in claim 1, wherein said effecters are pressing fingers.

3. The peristaltic pump as in claim 1, wherein said metal member is a magnetic material and said balancing member includes a metallic material.

4. The peristaltic pump as in claim 1, wherein said metal member is a metallic material and said balancing member includes a magnetic material.

5. The peristaltic pump as in claim 1, wherein said metal member is a magnetic material and said balancing member includes a magnetic material.

6. The peristaltic pump as in claim 1, wherein substantial countering of said reactive force by said balancing force is maintained in forth and backward movement of the effecters.

7. The peristaltic pump according to claim 1, wherein said balancing member produces a permanent magnetic field.

8. The peristaltic pump according to claim 1, wherein said balancing member is attracted to a magnetic field.

* * * * *